(12) United States Patent
Britz-McKibbin

(10) Patent No.: US 9,490,110 B2
(45) Date of Patent: Nov. 8, 2016

(54) MULTI-SEGMENT INJECTION-CAPILLARY ELECTROPHORESIS-MASS SPECTROMETRY (MSI-CE-MS): A MULTIPLEXED SCREENING PLATFORM AND DATA WORKFLOW FOR CHEMICAL ANALYSIS

(71) Applicant: McMaster University, Hamilton (CA)

(72) Inventor: Philip Britz-McKibbin, Hamilton (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 14/891,084

(22) PCT Filed: May 14, 2014

(86) PCT No.: PCT/CA2014/050454
§ 371 (c)(1),
(2) Date: Nov. 13, 2015

(87) PCT Pub. No.: WO2014/183217
PCT Pub. Date: Nov. 20, 2014

(65) Prior Publication Data
US 2016/0086780 A1    Mar. 24, 2016

Related U.S. Application Data

(60) Provisional application No. 61/822,951, filed on May 14, 2013.

(51) Int. Cl.
*H01J 49/26* (2006.01)
*H01J 49/00* (2006.01)
(Continued)

(52) U.S. Cl.
CPC ......... *H01J 49/0027* (2013.01); *G01N 27/447* (2013.01); *G01N 27/4473* (2013.01);
(Continued)

(58) Field of Classification Search
USPC ........................................ 250/281, 282, 288
See application file for complete search history.

(56) References Cited

U.S. PATENT DOCUMENTS 5,993,633 A  11/1999  Smith et al.
6,143,152 A  11/2000  Simpson et al.
(Continued)

OTHER PUBLICATIONS

Dhanaraju et al., "Capillary Electrophoresis—An insight into different modes and it's applications", Journal of Advanced Pharmacy Education & Research, vol. 4, Issue 1, pp. 1-12, Jan.-Mar. 2014.
(Continued)

*Primary Examiner* — Nicole Ippolito
(74) *Attorney, Agent, or Firm* — Bereskin & Parr LLP/S.E.N.C R.L., s.r.l

(57) ABSTRACT

Various embodiments illustrating a multiplexed method for high throughput screening of ions in biological samples within a single capillary when using capillary electrophoresis mass spectrometry (CE-MS) are illustrated. The method includes sequential injection of multiple sample segments in series within a single capillary, the sample segments being separated by a spacer plug of buffer, and multiplexed analysis of the sample segments simultaneously within a single capillary electrophoresis (CE) run. The method also includes application of voltage to the single capillary subsequent to sequential injection and zonal separation of polar metabolites within each sample segment by CE such that each analyte zone migrates within its characteristic electrophoretic mobility offset in time by the spacer. The incorporation of a quality control/reference sample and the use of dilution patterning with specific injection configurations also enables encoding of information temporally for enhanced data processing with quality assurance.

10 Claims, 7 Drawing Sheets

(51) Int. Cl.
  *G01N 27/447*  (2006.01)
  *H01J 49/04*  (2006.01)
  *H01J 49/16*  (2006.01)

(52) U.S. Cl.
  CPC .......... *H01J49/0404* (2013.01); *H01J 49/165* (2013.01); *G01N 27/44743* (2013.01); *G01N 27/44782* (2013.01)

(56) References Cited

U.S. PATENT DOCUMENTS

| | | | |
|---|---|---|---|
| 6,299,747 | B1 | 10/2001 | Dunayevskiy et al. |
| 6,524,456 | B1 | 2/2003 | Ramsey et al. |
| 6,833,919 | B2 | 12/2004 | Kenseth et al. |
| 6,837,977 | B1 | 1/2005 | Dunayevskiy et al. |
| 2006/0289059 | A1* | 12/2006 | Krylov ................ B01F 13/0072 137/7 |
| 2010/0111771 | A1 | 5/2010 | Gjerde et al. |
| 2011/0290648 | A1 | 12/2011 | Majlof et al. |

OTHER PUBLICATIONS

Sekhon, "An overview of capillary electrophoresis: Pharmaceutical, biopharmaceutical and biotechnology applications", J. Pham Educ Res, vol. 2, Issue No. 2, pp. 2-23, Dec. 2011.

* cited by examiner (a) Multiplexed Advantage of MSI-CE-MS: Single Run for Dilution Filter of Pooled QC (Plasma)

*Individual Plasma Metabolic Profiles of Naïve (Week 1) VS Trained (Week 6) at 3 Time Intervals*

MULTI-SEGMENT INJECTION-CAPILLARY ELECTROPHORESIS-MASS SPECTROMETRY (MSI-CE-MS): A MULTIPLEXED SCREENING PLATFORM AND DATA WORKFLOW FOR CHEMICAL ANALYSIS

FIELD

The described embodiments relate generally to screening of complex mixtures of ions in biological specimens, and particularly to screening of complex mixtures of ions in biological specimens when using capillary electrophoresis-mass spectrometry (CE-MS).

BACKGROUND

Separation science plays a key role for enhancing the performance of mass spectrometry (MS)-based analysis of complex biological samples in the field of emerging comprehensive metabolite profiling initiatives (i.e., metabolomics). A major challenge in metabolomics is the chemical diversity and wide dynamic range of the "metabolome" that remains largely uncharacterized. Consequently, high efficiency separations are used to provide greater selectivity, better quantitative reliability as well as higher quality mass spectra for qualitative identification becomes difficult to realize.

In various chromatographic techniques of separation (for example, liquid chromatography, gas chromatography etc.), sample throughput is limited since such techniques typically rely on a "single" sample injection. Consequently, the analysis time tends to be very long (for example, greater than 15 min per run). Furthermore, in such techniques, and especially when used in major metabolomics studies, major efforts are devoted to quality assurance (for example, quality control samples) and data pre-processing (for example, time alignment) to correct for long-term instrumental drift, which tend also to be time consuming, resource-intensive and subject to bias.

SUMMARY

Separation science plays a key role for enhancing the performance of mass spectrometry (MS)-based metabolomic studies. However, sample thoughput is limited when using conventional separation platforms with gradient elution involving a "single" sample injection. The disclosure herein discloses a multiplexed analysis based on multi-segment injection (MSI)-CE-MS that enhances sample throughput while improving data quality.

In a first aspect, some embodiments of the invention provide a method for screening of ions in biological samples within a single capillary when using capillary electrophoresis mass spectrometry (CE-MS), the method comprising: sequential injection of multiple sample segments in series within the single capillary, the sample segments being separated by a spacer plug of buffer; and multiplexed analysis of the sample segments simultaneously within a single capillary electrophoresis (CE) run.

In various embodiments, the method further comprises subsequent to sequential injection, application of voltage to the single capillary; and zonal separation of polar metabolites within each sample segment by CE such that each analyte zone migrates with its characteristic electrophoretic mobility offset in time by the spacer, and wherein the multiplexed analysis of two or more sample segments simultaneously within the single CE run that allows for desalting and resolution of isomers/isobars prior to ionization (ESI-MS).

In some embodiments, the method further comprises, carrying out data pre-processing methods to enhance data quality for untargeted screening of biological samples.

In some embodiments, the ions in the biological sample comprise a mixture of metabolites, peptides and or proteins.

In some embodiments, the biological sample is of animal, plant or human origin.

In some embodiments, the number of sample segments injected is less than seven segments. In some other embodiments, the number of sample segments injected is seven segments. In some further embodiments, the number of sample segments injected is more than seven segments.

In some embodiments, the alternating sequence of sample and spacer segments fills approximately a third of total capillary length of the single capillary.

In some embodiments, the number of sample segments injected is seven segments, and injection time for the seven sample segments is 5 seconds each, injection time for first six spacer plugs is 40 seconds, and injection time for seventh spacer plug is 5 seconds.

BRIEF DESCRIPTION OF THE DRAWINGS

A preferred embodiment of the present invention will now be described in detail with reference to the drawings, in which.

DESCRIPTION OF EXEMPLARY EMBODIMENTS

Figure 1:
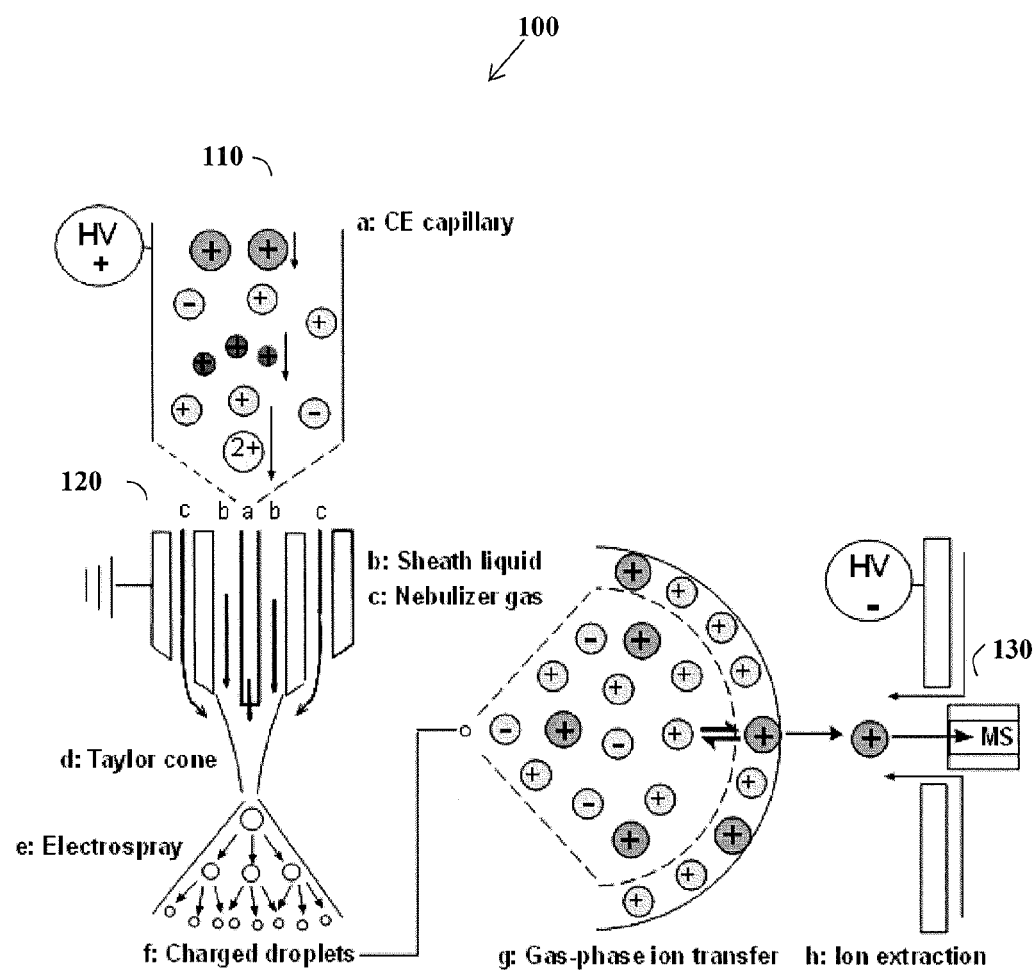
FIG. 1 illustrates a schematic of CE-MS system according to an example embodiment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about".

Further, the definitions and embodiments described are intended to be applicable to other embodiments herein described for which they are suitable as would be understood by a person skilled in the art. For example, in the passages herein, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

Described herein is an alternative MS-based separation platform that may enhance sample throughput while providing higher quality data for use in various fields, such as, for example, clinical medicine, drug development, biotechnology, environmental toxicology, and food safety, etc.

At present, CE-MS is used as a separation technique for polar and ionic metabolites that possess an intrinsic electrophoretic mobility under a specific buffer condition. Currently, most commercial CE-MS instruments utilize a coaxial sheath liquid interface that was first disclosed in U.S. Pat. No. 5,993,633 (Severs and Smith, 1997). To date, high-throughput screening by CE is achieved by performing separations massively "in-parallel" as exemplified by capillary array electrophoresis systems with laser-induced fluorescence detection for gene sequencing (N. J. Dovichi, J. Zhang Angew. Chem. Int. Ed. 2000, 39: 4463-4468.). Similar multiplexed approaches have also been developed for gene sequencing on microfluidic devices, as well as small molecule profiling by capillary array electrophoresis systems with UV absorbance detection as disclosed in U.S. Pat. No. 6,143,152 (Mathies et al., 1997) and U.S. Pat. No. 6,833,919 (Kenneth et al., 2002), respectively. However, these approaches achieve high sample throughput by utilizing an array of capillaries or multi-channel microfluidic systems with on-line photometric detection, where screening is performed "in parallel".

There are several disadvantages to the currently used approach. Examples of such disadvantages include complexity of array set-up, changes in ion migration times between capillaries due to differences in electroosmotic flow (EOF), inability to directly couple a capillary array system to electrospray ionization (ESI)-MS etc.

Accordingly, various embodiments of this disclosure relate to a separation platform based on multi-segment injection-capillary electrophoresis-mass spectrometry (MSI-CE-MS). In these embodiments, multiplexed analysis by CE is realized by injection of multiple sample plugs "in series" within a single capillary.

In other words, the invention, as described herein, is a multiplexed approach for the desalting, separation, detection and identification of ions (e.g., metabolites, peptides, protein) in complex mixtures based on the injection of a series of discrete sample segments displaced within a single capillary when using CE-MS.

Advantages of multi-segment injection may include enhanced sample throughput (for example, by over one order of magnitude), improved overall data quality for targeted or untargeted screening of metabolites, peptides and proteins etc., and increased opportunity to perform several unique experiments facilitating data processing relevant to untargeted screening, etc.

Reference is first made to FIG. 1, illustrating a CE-MS system 100 according to an example embodiment. CE-MS system 100 comprises a CE capillary 110 and a coaxial sheath liquid interface 120. The coaxial sheath liquid interface, as illustrated, is under positive ion mode for analyzing cations under acidic conditions. A similar configuration in CE-MS under negative ion mode is also used for analyzing anions under alkaline conditions.

In the illustrated capillary electrophoresis (CE) system, a homogenous aqueous buffer is used in CE capillary 110 for separations. An isocratic aqueous solution with organic solvent serves as a make-up flow in the sheath liquid, and mass calibrant ions are used for internal calibration of time of flight (TOF)-MS. This provides a stable spray environment throughout the separation in CE-MS. In a time of flight mass spectrometer (TOF-MS), ions accelerated by an electric field are injected into a flight space where no electric field or magnetic field is present. The ions are separated by their mass-to-charge ratio (m/z) according to their flight time in a drift tube until they reach a detector and are detected thereby.

In the embodiment of FIG. 1, ions are first separated in free solution by CE based on differences in their electrophoretic mobility. Ions migrating towards the distal end of the CE capillary 110 are then mixed with the sheath liquid and desorbed into the gas-phase by application of a high voltage at the emitter. Desorbed ions are then sampled into a capillary that leads to a MS 130 under vacuum, which resolves mixtures of ions based on their mass to charge ratio.

CE plays a key role in the resolution of isomers/isobars, preconcentration of dilute solutions and desalting of samples prior to ionization, whereas a high resolution MS (TOF-MS) functions as a multi-channel detector with fast data acquisition for mass resolution of co-migrating ions and signal generation. The constant composition of the buffer (CE) and sheath liquid flow (ESI-MS) allows for multiple sample plugs to be analyzed within the same capillary since ions migrate and ionize under steady-state conditions.

An example of equipment that may be used for CE-ESI-TOF/MS experiments includes Agilent G7100A CE system interfaced with coaxial sheath liquid electrospray ion source (Jet stream interface) to an Agilent 6230 TOF LC/MS orthogonal axis time-of-flight mass spectrometer. In this apparatus, nitrogen gas is used as the nebulizer gas in ESI and the drying gas for the MS and helium gas is used as a damping and collision gas. The system software for this apparatus is 3D-CE ChemStation (CE) and Agilent MassHunter Workstation Data Acquisition (TOF/MS). Data processing may be performed using MassHunter Qualitative and MassHunter Quantitative software. All data processing and electropherograms may be performed using Igor Pro 5.0 (Wavemetrics Inc., Lake Oswego, Oreg., USA).

Figure 2A:
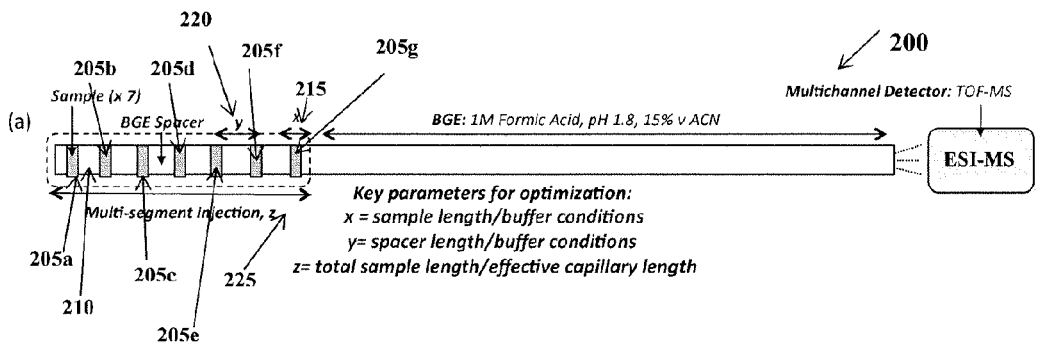
FIG. 2A illustrates an initial configuration of MSI-CE-MS sample plug according to an example embodiment.

Reference is next made to FIG. 2A, illustrating an injection sequence configuration 200 used in MSI-CE-MS according to an example embodiment. Injection sequence configuration 200 comprises a series of short injection segments 205a-205g of several identical samples containing a standard mixture of polar metabolites each displaced by a spacer 210. Spacer 210 is comprised of the homogeneous aqueous buffer present in the CE capillary.

In the illustrated embodiment, three key parameters are critical for optimization of MSI-CE-MS. These parameters include sample injection length/buffer conditions (x) 215, spacer plug length/buffer conditions (y) 220, as well as the total sample length of the injection relative to entire capillary length (z) 225.

In some cases, to maximize sample throughput, short sample injection plugs are used. In these cases, injection plugs with an optimum spacer length is used to allow for sufficient displacement of each sample segment for resolution of isomeric/isobaric ions prior to ionization. In some further cases, if greater sensitivity is desired, fewer sample plugs are introduced with a longer segment length (i.e., sample volume). This is used to allow for on-line preconcentration by CE. These variables are controlled by the duration and/or pressure setting used for hydrodynamic injection of samples in-capillary.

In various cases, the maximum number of samples that can be analyzed simultaneously by MSI-CE-MS depends on several factors, such as, for example, the complexity of the sample matrix, required resolution (targeted vs. untargeted screening), maximum voltage and total capillary length etc. In some cases, up to a third of the total capillary length is filled with multiple segments of samples and spacers in order to allow for sufficient peak capacity for isobaric resolution and desalting in the separation.

Figure 2B:
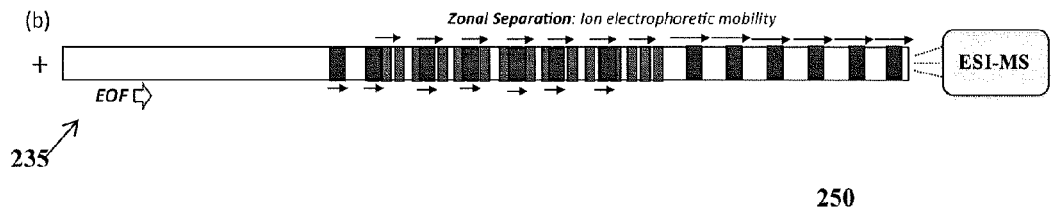
FIG. 2B illustrates a voltage application and zonal separation of polar metabolites within each sample plug of FIG. 2A.

Reference is next made to FIG. 2B, illustrating voltage application in CE 230. As illustrated, when voltage 235 is applied in CE, it results in zonal separation of ions 240 within each sample plug. Zonal separation 240 is dependent on intrinsic electrophoretic mobility of ions. However, ions with faster positive mobilities migrate well ahead of all other ions without co-migration (creatinine), whereas co-migration occurs for other ions with similar mobilities (Gln, Leu).

Figure 2C:
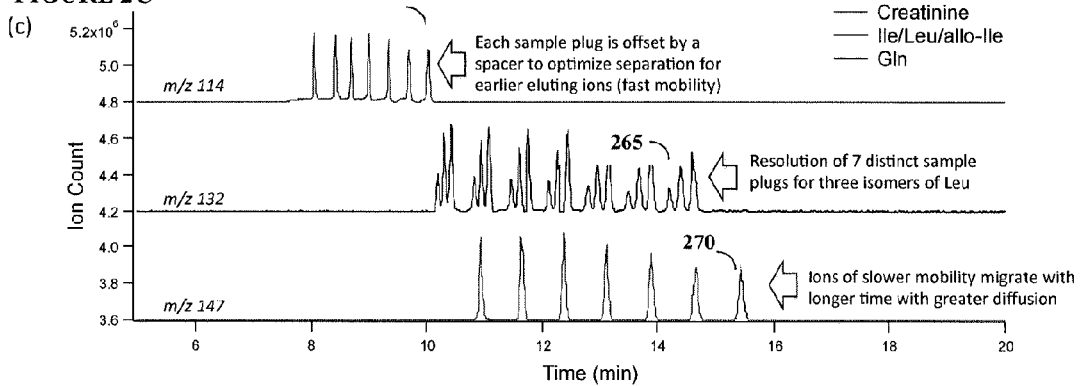
FIG. 2C illustrates a series of extracted ion electropherograms for multiplexed analysis of seven sample plugs according to an example embodiment.

FIG. 2C presents extracted ion electropherograms (EIEs) 250 for three representative polar metabolites and their isomers. Noteworthy, all ions are detected as a series of seven distinct peaks that are offset in time (<1 min per sample) as determined by the original spacer plug length.

As illustrated in EIE 260, each sample plug is offset by a spacer to optimize separation for earlier eluting ions with fast mobility. For example, as illustrated in EIE 265, the spacer was optimized in order to allow for sufficient time for baseline resolution of isomers within each sample segment, such as for resolution of three diastereomers of Ile, Leu and alto-Ile. Despite considerable peak overlap for Leu isomers and Gln, they are readily resolved when using TOF-MS as a high resolution mass analyzer due to differences in their mass over charge (m/z) ratio. EIE 270 illustrates that ions of slower mobility migrate with longer time with greater diffusion.

As illustrated in FIG. 2C, all ions migrate with a steady-state electrophoretic mobility with later eluting peaks undergoing more band broadening due to longitudinal diffusion. Accordingly, MSI-CE-MS offers a simple yet multiplexed approach for simultaneous analysis of seven or more sample plugs within a single capillary without any modification to the instrumentation while retaining isomeric resolution.

Figure 3:
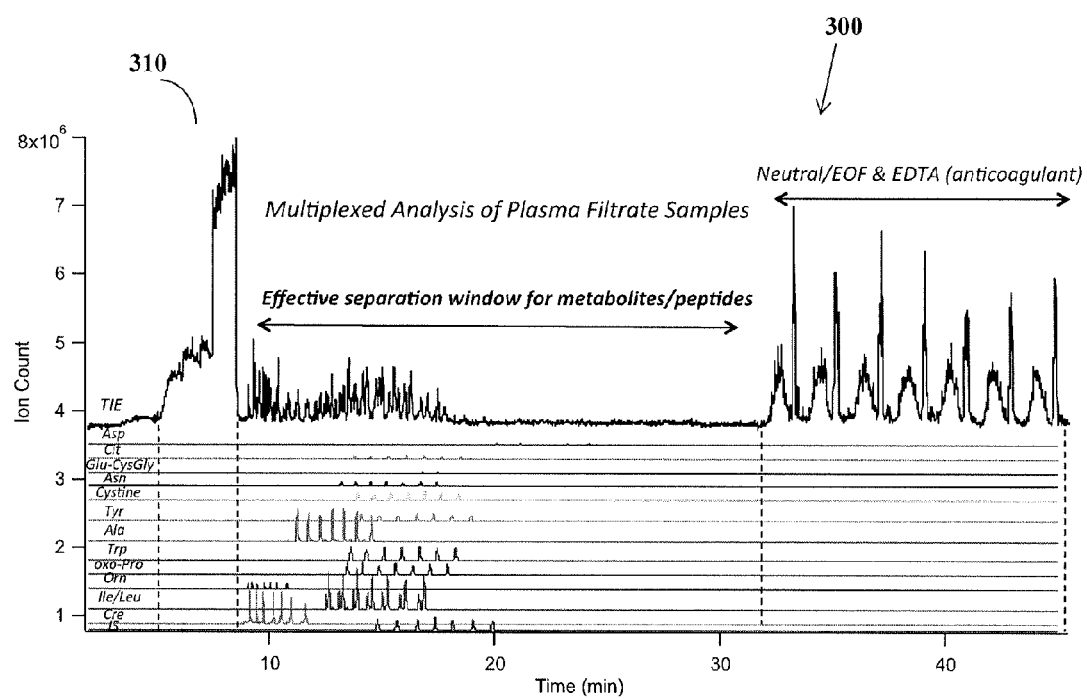
FIG. 3 illustrates a total ion electropherogram (TIE) representation of multiplexed analysis of seven identical human plasma filtrate samples within a single separation.

Reference is next made to FIG. 3, which illustrates a multiplexed analysis 300 of human plasma filtrate using a "7 segment sample injection" format. In one embodiment, human plasma filtrate is prepared by collecting EDTA-treated blood on ice, diluting fractionated plasma two-fold in buffer, and centrifuging using a 3 kDa MWCO filter. Other ways of preparing human plasma filtrate may also be used.

In some embodiments, human plasma filtrate is prepared by collecting human blood in 6 mL EDTA-coated vacutainer. The vacutainer is kept on ice until centrifugation. Centrifugation may be carried out for 10 minutes at 4000 rpm @ 4° C. The centrifuged plasma is then removed and frozen at −80° C. until analysis. The human plasma specimen is then slowly thawed and then diluted. The specimen may be diluted 2-fold in 100 mM ammonium acetate, pH 5, vortexed for 30 s. The specimen is then ultrafiltrated. Ultrafiltration may occur using a molecular weight cut-off (MWCO 3 kDa) for 10 minute×4500 rpm. About ~30 µL of the two-fold diluted human plasma filtrate may then be analyzed by MSI-CE-MS with L-glutamine methylester and 3-chloro-L-tyrosine (50 µM) as internal standards (IS).

Once the human plasma filtrate is prepared, the seven identical sample plugs of the filtrate is introduced into the capillary with a similar configuration as shown in FIG. 2A. The total ion electropherogram (TIE) 310, as illustrated, highlights that MSI-CE-MS allows for effective desalting of involatile ions in plasma, including inorganic ions migrating as a broad zone from 4-8 minutes (e.g., Na+) prior to elution of low abundance polar metabolites (ornithine, Orn) and their isomers (Ile, Leu) that are detected as a series of 7 discrete peaks. Under these conditions, various classes of cationic metabolites are directly analyzed from complex biofluids with higher sample throughput, including amines, amino acids, peptides and their isomers. Also, neutral metabolites and excess EDTA (used as anticoagulant) that migrate after 32 minutes are well resolved from polar metabolites that prevent deleterious ion suppression. Thus, the effective separation window that allows for reliable quantification of low abundance plasma metabolites/peptides ranges from 8 until 32 minutes with the majority of analytes migrating within 20 minutes as highlighted in the TIE. Unlike direct injection-ESI-MS, MSI-CE-MS provides the advantages of improved selectivity (resolution of isobars/isomers), and reduced ion suppression (separation of involatile ions) while allowing for reliable quantification of low abundance metabolites. In some cases, an internal standard (IS) is introduced within each sample plug to correct for variations in sample injection volume that is needed for reliable quantification.

Figure 4:
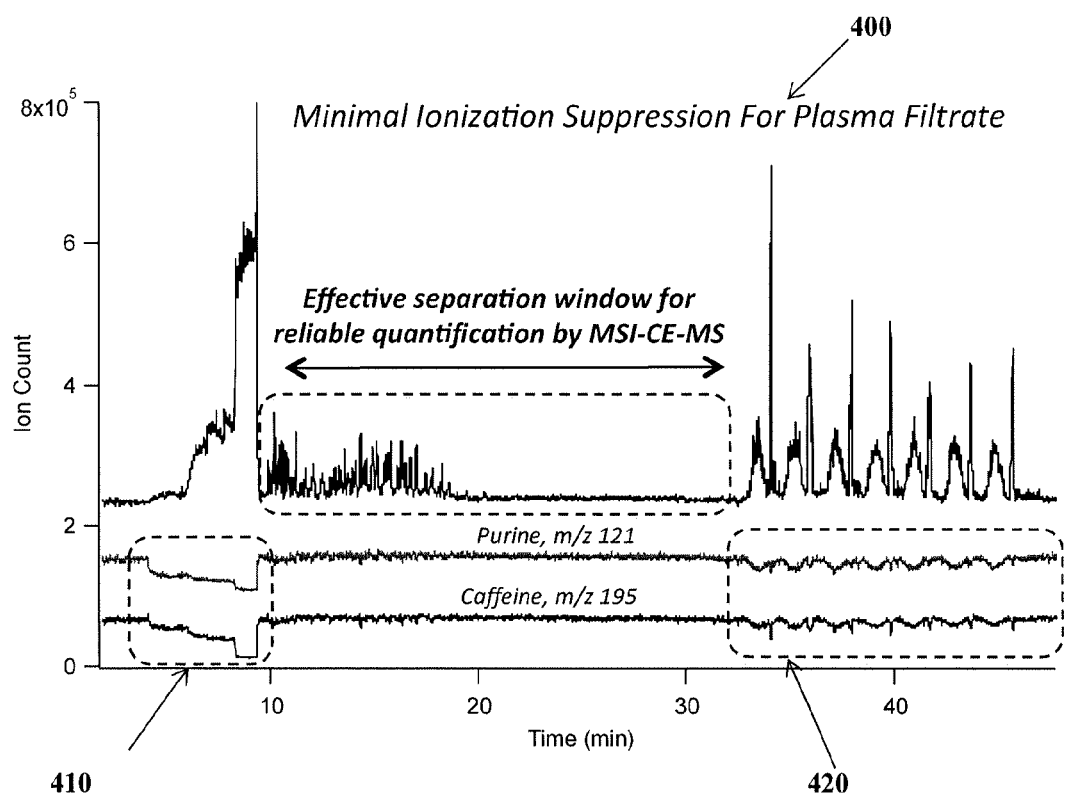
FIG. 4 illustrates an overlay of TIE for multiplexed analysis of seven identical plasma filtrate samples without ion suppression along with two EIEs for purine and caffeine according to an example embodiment.

Reference is next made to FIG. 4, which illustrates a graphical representation 400 comprising overlay of TIE with EIE. In particular, FIG. 4 illustrates an overlay of TIE for multiplexed analysis of seven identical plasma filtrate samples in series with MSI-CE-MS along with extracted ion electropherograms (EIEs) for two ions added in the sheath liquid for mass calibration of TOF-MS. In the illustrated embodiment, the two ions added in the sheath liquid include purine and caffeine.

As illustrated, there are two distinct time regions 410 and 420 showing evidence of ion suppression. Region 410 reflects lower signals (ion counts) for both purine and caffeine that corresponds to the salt front (4-9 minutes) and region 420 reflects lower signals (ion counts) for both purine and caffeine that corresponds to electroosmotic flow (32-50 minutes).

Under these conditions, plasma metabolites that migrate between 9 and 30 minutes are quantified without ion suppression effects with the majority of ions detected under 20 minutes. The effective separation of involatile interferences derived from multiple sample segments prior to ionization enables direct quantification of metabolites in complex sample matrices without the need for stable isotope internal standards.

Figure 5A:
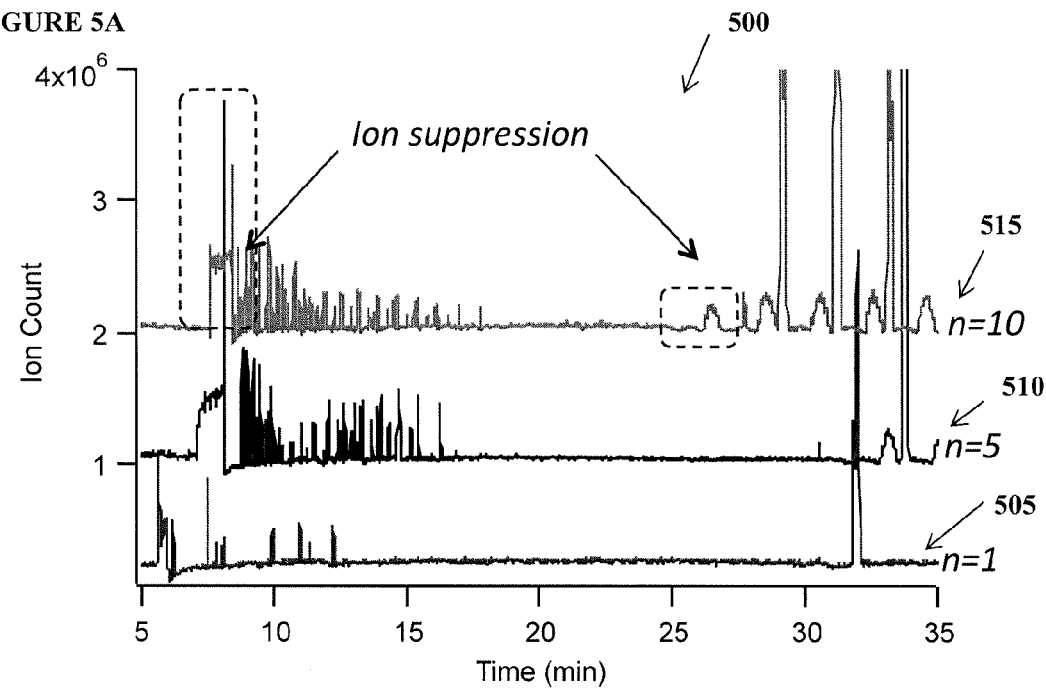
FIG. 5A illustrates an overlay of TIE using one, five and ten discrete sample plugs of plasma filtrate according to an example embodiment.

Reference is made to FIG. 5A illustrating overlay of TIEs 500 measured by TOF-MS. In particular, FIG. 5A illustrates TIE 505 when using one plasma filtrate sample, TIE 510 when using five identical plasma filtrate samples and TIE 515 when using ten identical plasma filtrate samples. FIG. 5A allows for a comparison of performance of MSI-CE-MS when using one, five and ten identical plasma filtrate samples injected as distinct segments in series with the same spacer within the capillary.

Figure 5B:
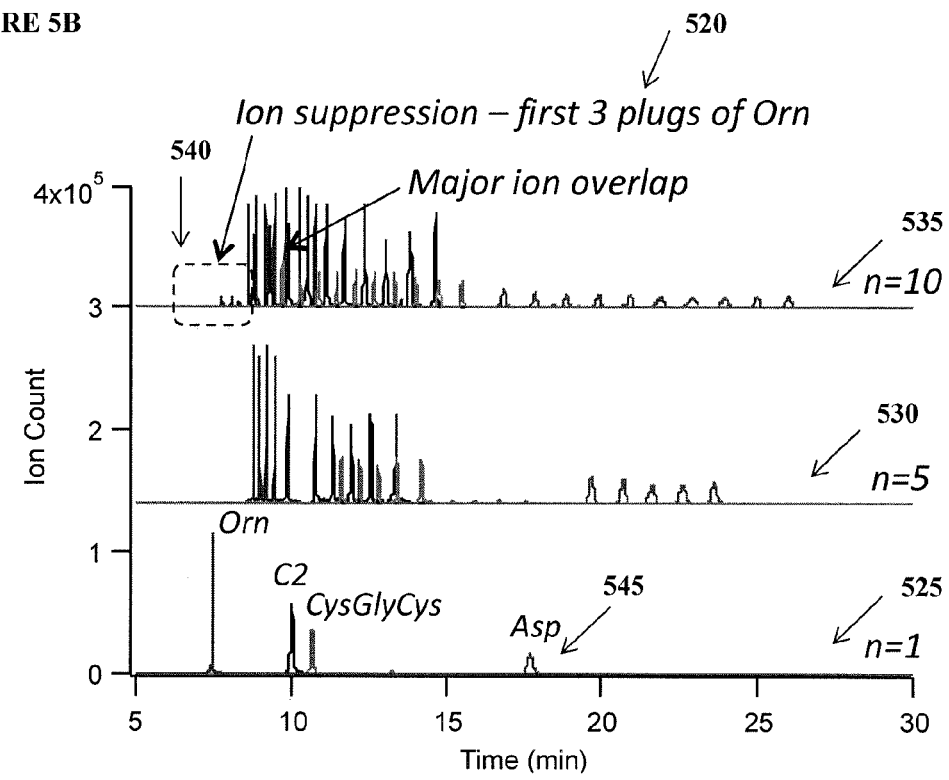
FIG. 5B illustrates a series of EIEs for representative plasma metabolites with different mobilities when using one, five and ten discrete sample plugs according to an example embodiment.

FIG. 5B illustrates an overlay of EIEs 520 for four cationic metabolites when using one, five and ten identical plasma filtrate samples. Four representative cations, as illustrated, comprise L-ornithine (Orn), O-acetyl-L-carntine (C2), Cys-GlyCys mixed disulfide and L-aspartic acid (Asp). EIE 525 corresponds to one plasma filtrate sample, EIE 530 corresponds to five identical plasma filtrate samples, and EIE 535 corresponds to ten identical plasma filtrate samples.

EIE 535 illustrates that considerable overlap exists in the case of a "ten segment" injection format. In EIE 535, the first three Orn peaks 540 undergo major signal suppression unlike the remaining seven peaks due to their overlap with the early migrating salt front. Similarly, in EIE 525, the late migrating Asp peaks 545 begin to co-migrate with the first EOF zones. However, this does not generate significant ion suppression.

A comparison of FIGS. 5A and 5B illustrate that there is insufficient peak capacity and a more narrow separation time window for resolving some early eluting ions that co-migrate with the salt front when using a ten plug series injection. In some cases, longer total capillary lengths (>1.2 m) may be used to accommodate a larger number of sample segments without exceeding a third of the total capillary length. However, in most cases, a maximum voltage setting for commercial CE instrumentation is limited to 30 kV. In such cases, longer capillaries result in a lower electric field strength, which leads to longer analysis times and excessive band dispersion that deteriorates the separation and isomeric resolution.

In various embodiments illustrated herein, the number of sample segments introduced into the capillary affects the effective capillary length needed for separation. If a large number of sample segments are introduced into the capillary, the effective capillary length needed for separation decreases, which results in a more narrow separation window and considerable overlap of fast and slow migrating ions with the salt front and electroosmotic flow (EOF), respectively. Accordingly, an average of seven sample segments may be used.

Figure 6A:
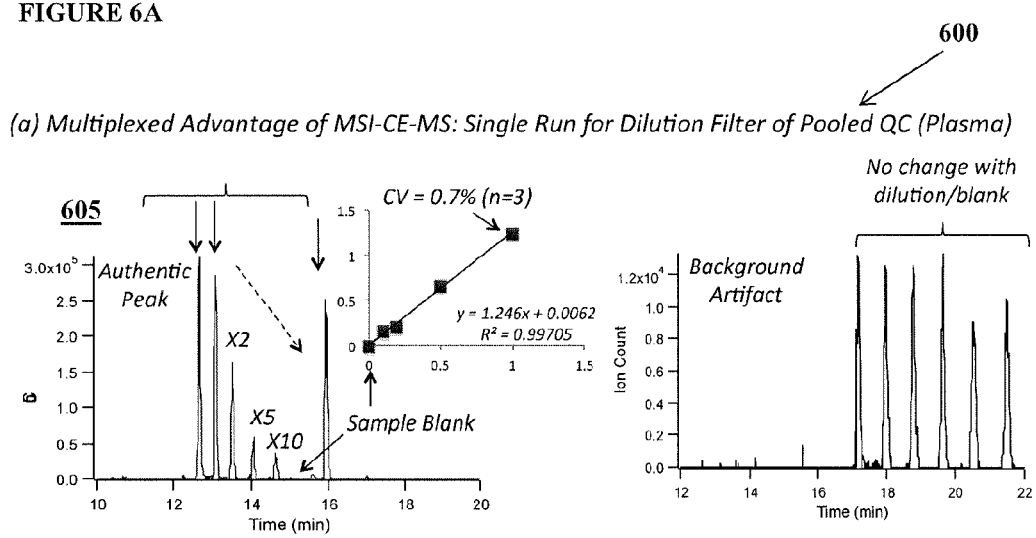
FIG. 6A illustrates a graphical representation of a serial dilution filter approach for identification of authentic peaks in a pooled plasma filtrate sample according to an example embodiment.

Reference is next made to FIG. 6A, illustrating as a graphical representation 600 of a serial dilution filter approach for identification of authentic peaks in a pooled plasma filtrate sample. In this illustration, a pooled plasma sample, similar to that used in illustration of FIG. 3, is injected as a series of discrete samples using a "7 segment" format with the first, second and seventh sample segment being the same undiluted sample. This experiment is carried out to assess reproducibility (triplicate, n=3). Next, a series of dilution of the plasma sample are injected as the third (two-fold), fourth (5-fold) and fifth (10-fold) segment along with a blank (buffer filtrate devoid of plasma) sample comprising the sixth segment. This is one example of applying MSI-CE-MS in a data workflow when using a serial injection configuration and specific dilution patterning to encode information temporally via signal pattern recognition.

Typically, a major fraction of signals detected in ESI-MS are artifact peaks derived from various salt adducts, solvent clusters and impurities present in solvent/buffers, which can lead to false discoveries in untargeted screening. FIG. 6A illustrates that a single run can be used to unambiguously identify "authentic" peaks 605 that are reproducibly detected (CV<10%), undergo a linear dependence in response with dilution ($R^2$>0.99) whereas no signal is detected in the blank, which would normally take several hours to complete when using conventional LC-MS based on single injections.

Moreover, more reliable data can be derived from MSI-CE-MS without complicated time alignment and data pre-processing requirements since peaks are readily recognized as a distinct pattern within a 5 minute offset. In contrast, artifact peaks are reflected by a constant signal measured across all segments injected (including blank) as shown in FIG. 5A. Accordingly, a serial dilution filter approach provides a simple way to derive a list of authentic peaks derived from the sample of interest while excluding background ions that can contribute to data over-fitting and bias when using multivariate analysis in untargeted screening, such as metabolomics.

Figure 6B:
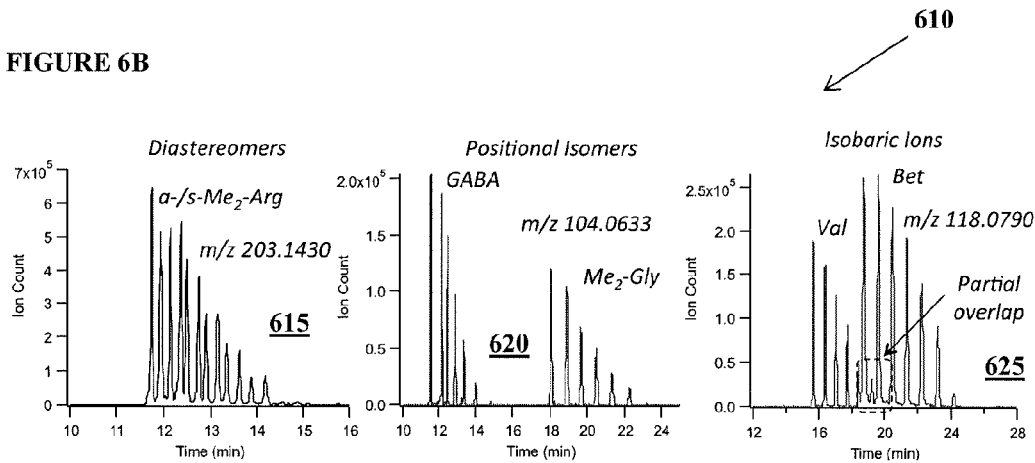
FIG. 6B illustrates a 7-point calibration curve for a serial dilution of metabolite standards (including a blank) within a single run seven plug format according to an example embodiment.

FIG. 6B illustrates that MSI-CE-MS can be used as a multiplexed method to acquire a 7-point calibration curve 610 from a serial dilution of metabolite standards (including a blank) within a single run, including isobaric/isomeric ions that are resolved by CE prior to ionization. As illustrated in 615, i.e. in the case of diastereomers (symmetric and asymmetric dimethylarginine), and as illustrated in 620, i.e. in the case of positional isomers with different $pK_a$ (γ-amino butyric acid and sarcosine/dimethylglycine), all peaks from different segments can be readily resolved from each other. As illustrated in 625, in the case of certain isobars/isomers with intermediate differences in mobility (valine and betaine), partial overlap for some sample segments can occur. The partial overlap of some sample segments may result from using a large number of sample segments injected in series within a single capillary. This situation may be improved by either injecting fewer segments or using longer capillaries at higher voltages to provide greater peak capacity for the separation.

Figure 7A:
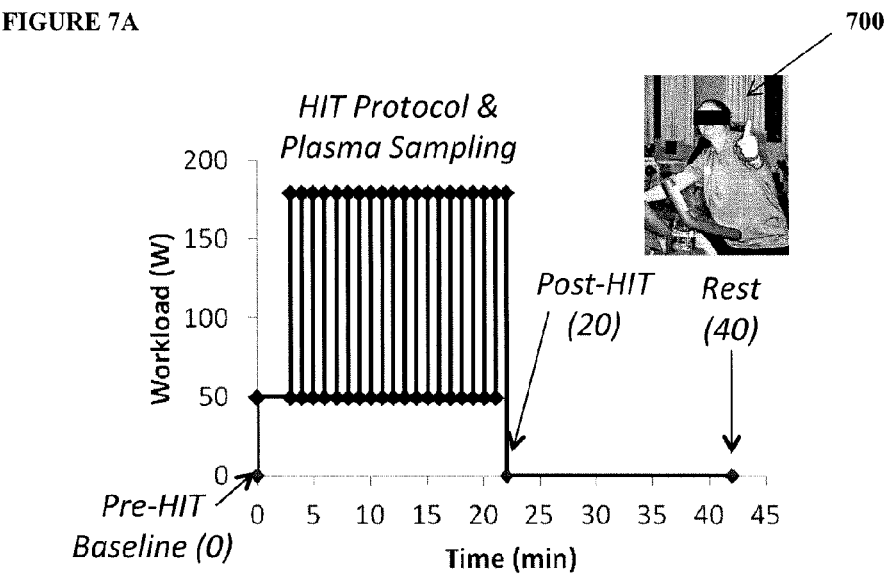
FIG. 7A illustrates the application of MSI-CE-MS as a multiplexed screening tool for metabolomics involving the assessment of time-dependent changes in metabolism of individual subjects involved in exercise training according to an example embodiment.

Reference is next made to FIG. 7A illustrating the application of MSI-CE-MS as a multiplexed screening tool for metabolomics involving the assessment of time-dependent changes in metabolism of individual subjects involved in exercise training. This illustration is based on an experiment where a group of subjects performed a six week high intensity interval training (HIT) protocol involving a series of intermittent yet high intensity ergometer cycling over 20 minute with plasma samples acquired, as illustrated in 700, at three time intervals (pre-HIT [0], post-HIT [20 minute] and recovery [40 minute]) at week 1 (untrained/naïve) and week 6 (trained/adaptive response) of the intervention under standardized conditions (same workload).

Figure 7B:
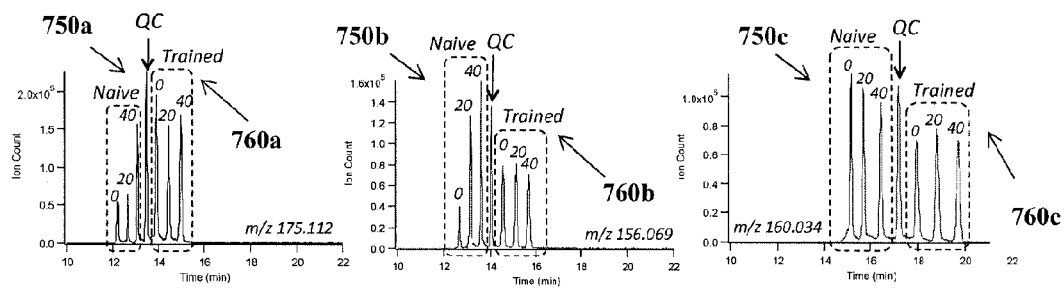
FIG. 7B illustrates a multiplexed analysis of dynamic changes in plasma metabolism from an individual subject to exercise training illustrated in FIG. 7A.

FIG. 7B illustrates that MSI-CE-MS allows for relative quantification of changes in plasma metabolites for each individual when using a "7 segment injection" with the first three samples 750a, 750b, 750c represent week 1 of HIT intervention (naïve/untrained) and the last three segments 760a, 760b, 760c injected represent week 6 of trial (trained). As illustrated in each graph, between samples 750a-750c and 760a-760c, respectively, a pooled quality control (QC) is included as the fourth sample segment, which allows for assessment of instrument drift over time while also providing a reference for comparing individual changes in metabolism to average responses of the group.

Putative plasma markers of exercise-induced oxidative stress as well as adaptive training response can be identified by comparing changes in metabolites as a function of time. In most cases, plasma metabolites remain stable for the trained subject relative to increases in peak responses for certain ions (m/z 175.112 and m/z 156.069) after HIT (20 minutes) and/or recovery (40 minutes). Thus, pattern recognition methods offer a simple way to process multiplexed MSI-CE-MS data sets more efficiently than the conventional "metabolomics workflow" that involves intensive data pre-processing and time alignment of separate LC-MS, GC-MS or CE-MS runs involving individual samples.

Moreover, due to the higher throughput of MSI-CE-MS involving a single instrumentation, untargeted screening can be completed within a shorter time period (>400 samples per day including QCs) thus ensuring greater stability and overall robustness. This methodology is also applicable to other sample types (e.g., plasma, urine, saliva, sweat, dried blood extracts, tissue extracts) and anionic small molecules (e.g., organic acids, sugar phosphates, nucleotides) under alkaline conditions and negative ion mode detection, as well as other classes of ions that can be separated by CE, including drugs, pollutants, nutraceuticals, peptides, glycans and protein.

Discussed below is an example CE-CSI-TOF/MS experimentation performed using Agilent G7100A CE system interfaced with coaxial sheath liquid electrospray ion source to an Agilent 6230 TOF LC/MS orthogonal axis time-of-flight mass spectrometer. In this experiment, the sheath liquid is 0.1% v formic acid in 60:40 MeOH:H$_2$O at a flow rate of 10 μL/min. The mass spectrometer is operated in positive-ion mode with a Vcap of 2000 V, a nozzle voltage of 2000 V, a drying gas temperature at 300° C., a drying gas flow rate of 8 L/min, a nebulizer gas (N$_2$) pressure of 10 psi, a sheath gas temperature at 195° C., and a sheath gas flow rate of 3.5 L/min.

The MS settings for ion extraction include fragmentor=−145 V, skimmer=−65 V and Oct 1 RF Vpp=750 V. The TOF-MS monitored ions over a mass range m/z 50-1000 with 6800 transients/scan. Purine and hexakis (2,2,3,3-tetrafluoropropoxy)phosphazine (HP-0921) are spiked into the sheath liquid at a concentration of 0.02% v and produced corresponding reference ions at m/z 119.03632 and 981.9956 that were used for real-time internal mass-correction allowing for mass accuracy <2 ppm in most cases.

An uncoated fused-silica capillary, such as one from Polymicro Technologies, with a 50 μm internal diameter and 100 cm total length is used in this experiment. For additional resolution and peak capacity a total capillary length of 120 cm can also be used. The capillary is maintained at 20° C. 1 M formic acid, pH 1.8 with 15% v acetonitrile is used as the background electrolyte (BGE) for CE separation using an applied voltage of 30 kV, as well as the spacer used to segment multiple sample plugs within the capillary during sample injection. It is critical that the capillary is washed and conditioned extensively with solvents and background electrolyte prior to first usage.

The optimum multi-segment injection configuration used for multiplexed analysis of plasma filtrate samples in this experiment consisted of an alternating sequence of hydrodynamic injections at 100 mbar pressure of sample (5 s) followed by BGE spacer (40 s) with the exception of the final BGE spacer (5 s). When using a seven or more sample plug format in MSI-CE-MS, the sample injection configuration thus consisted of the following sequence:

1) 5 s sample with 40 s BGE spacer
2) 5 s sample with 40 s BGE spacer
3) 5 s sample with 40 s BGE spacer
4) 5 s sample with 40 s BGE spacer
5) 5 s sample with 40 s BGE spacer
6) 5 s sample with 40 s BGE spacer
7) 5 s sample with 5 s BGE spacer Thus, the total injection time is 280 s (4.67 min) at 100 mbar, which is equivalent to an injection length consisting of alternating sample segments and spacer that fills approximately 34% of the total capillary length. In order to re-condition the capillary between sample runs, a rinsing program was performed for 600 s (10 min) at high pressure (1000 mbar) using the BGE.

Various different configurations of MSI-CE-MS ranging using 2 to 10 or more sample segment injections may also be used. The number of sample segment injections may depend on the desired sample throughput, sensitivity requirements, as well as nature of the biological specimen. In various cases, a 7 sample plug format is used in MSI-CE-MS since it offers the highest sample throughput under a reasonable time frame (<25 min) without deleterious band broadening while allowing for resolution of major isomers (Ile/Leu) without signal suppression form excess inorganic ions (Na$^+$).

However, the injection sequence can be readily varied to achieve greater sensitivity by reducing the number of sample segment (to 3) with longer sample injection volumes (50 s at 100 mbar) with same spacer (40 s at 100 mbar) such that it occupies the same effective capillary length (34%). Although larger numbers of sample plugs (>10) could be accommodated with the use of longer total capillary lengths, this is currently limited by the maximum voltage setting of the CE instrument (30 kV), such that long capillary lengths beyond 120 cm have lower electric field strengths resulting in broad peaks with long migration times. The availability of high voltage sources (40-50 kV) in conjunction with longer capillaries in CE-MS would further enhance peak capacity such that further increases in sample throughput (>10 samples per run) could be achieved even when applied to complex biological samples.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

I claim:

1. A method for screening of ions in biological samples within a single capillary when using capillary electrophoresis mass spectrometry (CE-MS), the method comprising:
   sequential injection of multiple sample segments in series within a single capillary, the sample segments being separated by a spacer plug of buffer;
   multiplexed analysis of the sample segments simultaneously within a single capillary electrophoresis (CE) run subsequent to sequential injection, application of voltage to the single capillary; and
   zonal separation of polar metabolites within each sample segment by CE so that each analyte zone migrates within its characteristic electrophoretic mobility offset in time by the spacer, so that the multiplexed analysis of two or more sample segments simultaneously within the single CE run to allow for desalting and resolution of isomers/isobars prior to ionization (ESI-MS).

2. The method of claim 1, further comprising:
   carrying out data pre-processing methods with quality assurance for untargeted screening of biological samples.

3. The method of claim 2, wherein the data pre-processing methods comprise a quality control/reference sample and the use of specific injection configurations with dilution patterning to encode information temporally via signal pattern recognition.

4. The method of claim 1, wherein the ions in the biological sample comprise a mixture of metabolites, peptides and or proteins.

5. The method of claim 1, wherein the biological sample is of animal, plant or human origin.

6. The method of claim 1, wherein the number of sample segments injected is less than seven segments.

7. The method of claim 1, wherein the number of sample segments injected is seven segments.

8. The method of claim 1, wherein the number of sample segments injected is more than seven segments.

9. The method of claim 1, wherein the alternating sequence of sample and spacer segments fill approximately a third of total capillary length of the single capillary.

10. The method of claim 1, wherein the number of sample segments injected is seven segments, and wherein injection time for the seven sample segments is about 5 seconds each, injection time for first six spacer plugs is about 40 seconds, and injection time for seventh spacer plus is about 5 seconds.

* * * * *